United States Patent
Krupnik et al.

(10) Patent No.: US 10,568,714 B2
(45) Date of Patent: Feb. 25, 2020

(54) CONTROLLING OPACITY OF FLUOROSCOPE MARKERS

(71) Applicant: Biosense Webster (Israel) Ltd., Yokneam (IL)

(72) Inventors: Ronen Krupnik, Karmiel (IL); Natan Sharon Katz, Atlit (IL); Roy Urman, Karkur (IL)

(73) Assignee: BIOSENSE WEBSTER (ISRAEL) LTD., Yokneam (IL)

(*) Notice: Subject to any disclaimer, the term of this patent is extended or adjusted under 35 U.S.C. 154(b) by 379 days.

(21) Appl. No.: 15/176,583

(22) Filed: Jun. 8, 2016

(65) Prior Publication Data

US 2017/0007354 A1    Jan. 12, 2017

Related U.S. Application Data

(60) Provisional application No. 62/190,291, filed on Jul. 9, 2015.

(51) Int. Cl.
*A61B 90/00* (2016.01)
*A61B 6/00* (2006.01)
*A61B 17/00* (2006.01)

(52) U.S. Cl.
CPC .............. *A61B 90/39* (2016.02); *A61B 6/487* (2013.01); *A61B 2017/0092* (2013.01); *A61B 2090/376* (2016.02); *A61B 2090/3933* (2016.02); *A61B 2090/3966* (2016.02)

(58) Field of Classification Search
USPC .......................................... 600/431; 359/296
See application file for complete search history.

(56) References Cited

U.S. PATENT DOCUMENTS

| | | | | |
|---|---|---|---|---|
| 2007/0268556 | A1* | 11/2007 | Chopra | G02F 1/167 359/296 |
| 2010/0123096 | A1* | 5/2010 | Suzuki | H01M 4/131 252/182.1 |
| 2011/0165462 | A1* | 7/2011 | Zhamu | H01M 4/134 429/223 |
| 2016/0349381 | A1* | 12/2016 | Friedman | G01T 1/185 |

FOREIGN PATENT DOCUMENTS

| EP | 1942662 A1 | 7/2008 |
|---|---|---|
| WO | 2012090148 A1 | 7/2012 |

OTHER PUBLICATIONS

European Search Report dated Nov. 21, 2016 for EP 16 17 8562.
Lattuada, M. et al. Synthesis, Properties and Applications of Janus Nanoparticles. Nano Today (2011) 6, 286-308.
U.S. Appl. No. 62/190,291, filed Jul. 9, 2015.

* cited by examiner

*Primary Examiner* — Nicole F Lavert
(74) *Attorney, Agent, or Firm* — Notaro, Michalos & Zaccaria P.C.

(57) ABSTRACT

Apparatus, consisting of an envelope transparent to X-rays, and a fluid transparent to X-rays and contained within the envelope. Multiple charged particles, opaque to X-rays, are suspended within the fluid. There are at least two electrodes on opposite sides of the envelope, that are configured to apply a field to the multiple particles, so that, absent the field, the particles disperse throughout the fluid.

22 Claims, 6 Drawing Sheets

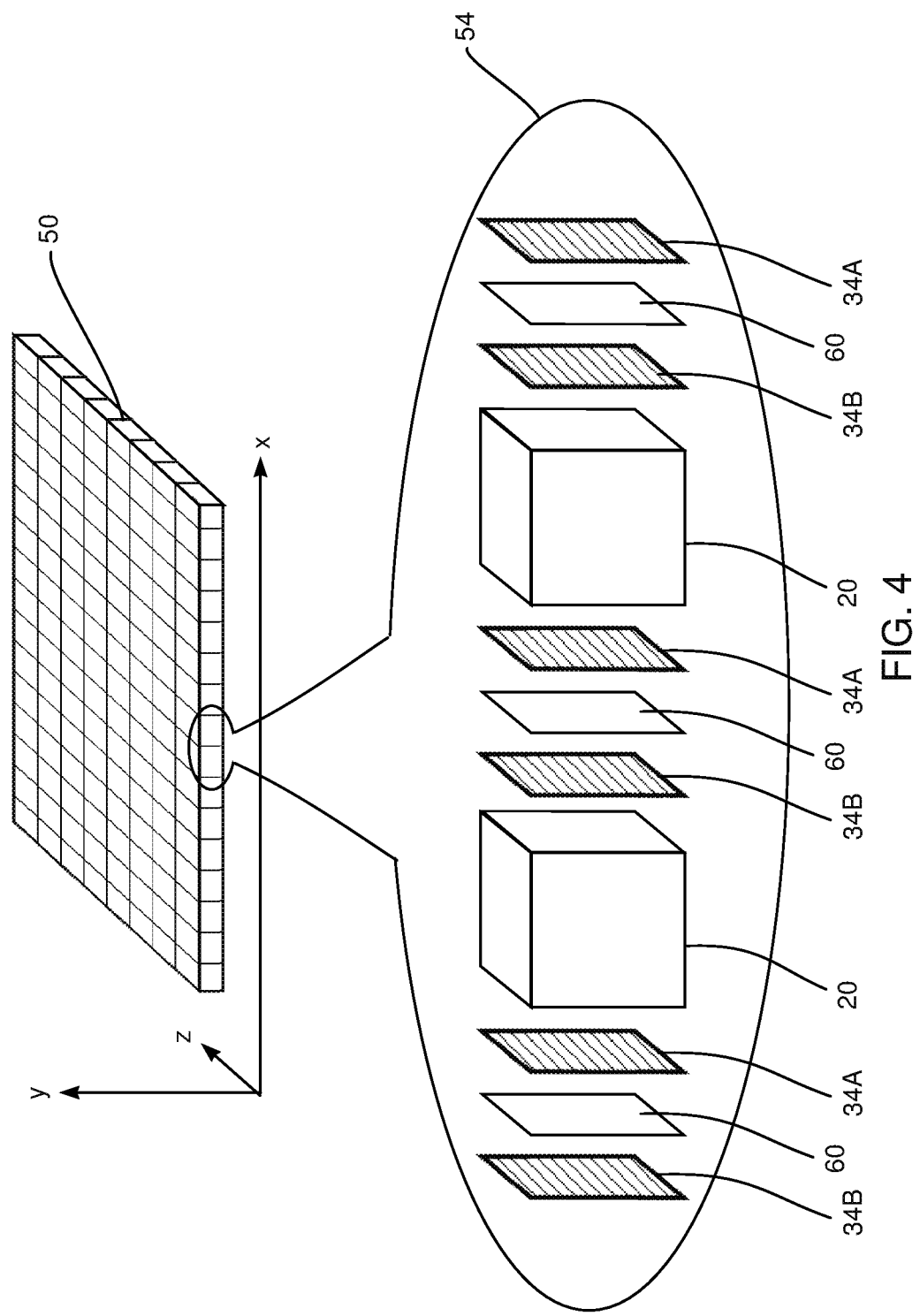

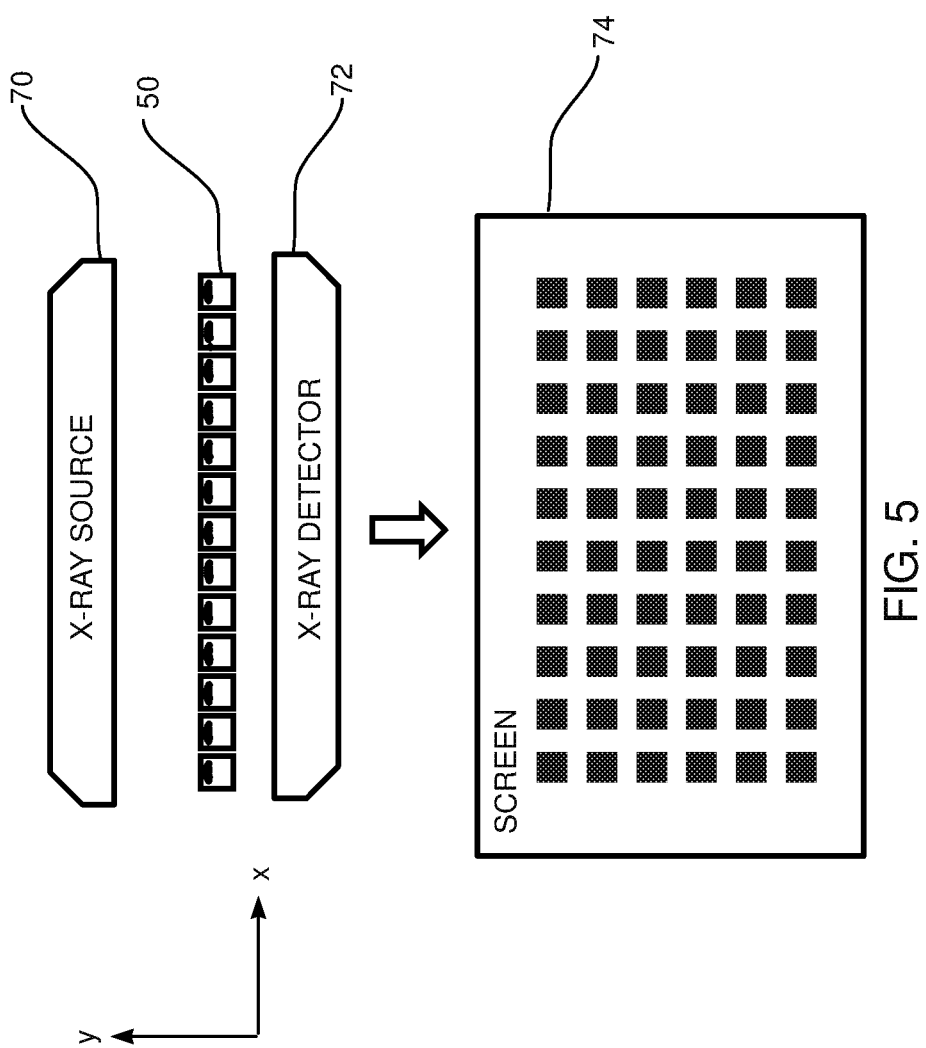

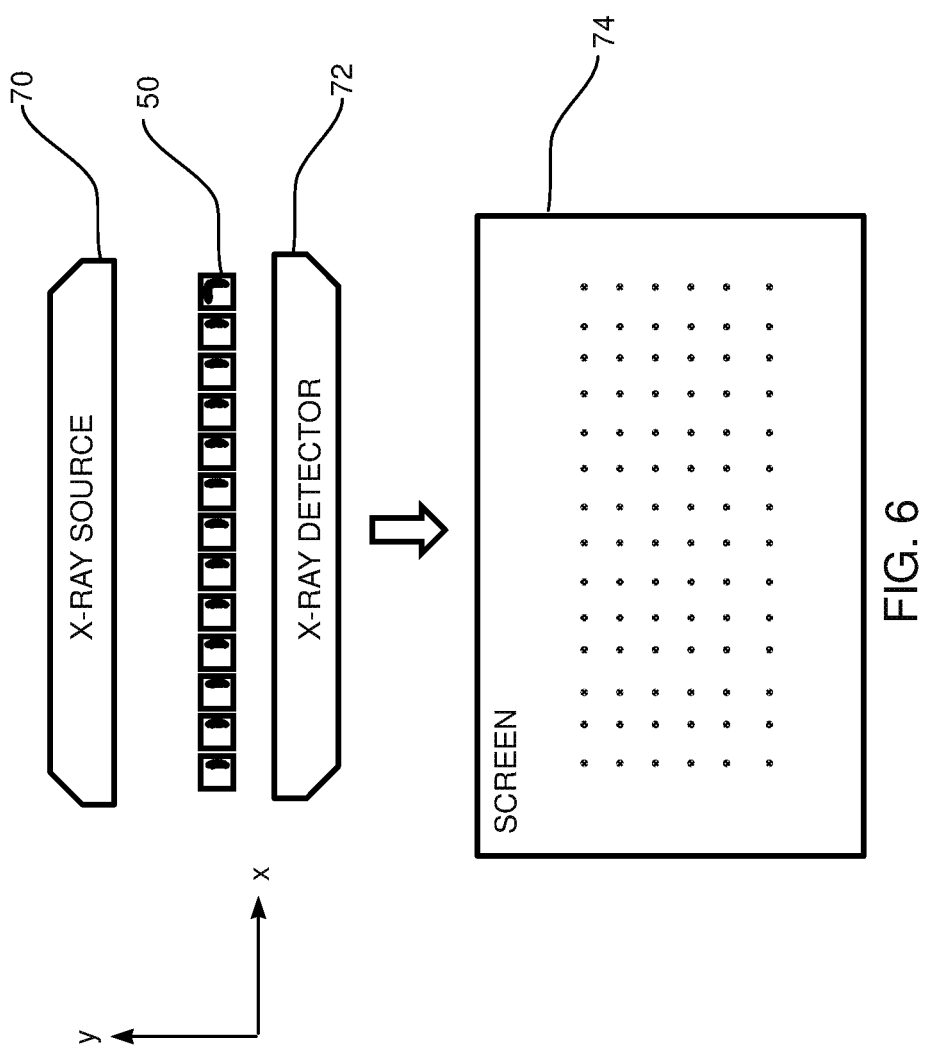

CONTROLLING OPACITY OF FLUOROSCOPE MARKERS

CROSS-REFERENCE TO RELATED APPLICATION

This application claims the benefit of U.S. Provisional Patent Application 62/190,291, filed Jul. 9, 2015, which is incorporated herein by reference.

FIELD OF THE INVENTION

The present invention relates generally to fluoroscopy, and specifically to the design and operation of fluoroscope markers that can have controllable opacity.

BACKGROUND OF THE INVENTION

During a fluoroscopy procedure, a physician performing the procedure may need to indicate a specific region of an image generated by the fluoroscopy. Typically, the indication may be implemented by the physician positioning a fluoroscopically opaque marker in an appropriate location of the region being imaged. Once the indication has been registered within the image, the physician may remove the marker.

The positioning and removal of the marker take time, and also detract from the concentration of the physician performing the procedure.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides apparatus, including:
 an envelope transparent to X-rays;
 a fluid transparent to X-rays and contained within the envelope;
 multiple charged particles, opaque to X-rays, suspended within the fluid; and
 at least two electrodes on opposite sides of the envelope, configured to apply a field to the multiple particles, and wherein absent the field, the particles disperse throughout the fluid.

In a disclosed embodiment the field applied by the at least two electrodes attracts the multiple charged particles to form a layer within the envelope so as to render the envelope opaque to the X-rays, or alternatively the field applied by the at least two electrodes attracts the multiple charged particles to form a layer within the envelope so as to render the envelope transparent to the X-rays.

In a further disclosed embodiment the at least two electrodes on opposite sides of the envelope consist of a first pair of electrodes on a first pair of opposite sides of the envelope and a second pair of electrodes on a second pair of opposite sides of the envelope, and the first and the second pairs of electrodes are mutually orthogonal. Typically, the first pair of electrodes is configured to apply a first field so as to attract the multiple charged particles to form a first layer within the envelope that renders the envelope opaque to the X-rays, and the second pair of electrodes is configured to apply a second field so as to attract the multiple charged particles to form a second layer within the envelope that renders the envelope transparent to the X-rays.

There is further provided, according to an embodiment of the present invention, apparatus, including:
 an array of envelopes transparent to X-rays;
 a fluid transparent to X-rays and contained within the receptacles;
 multiple charged particles, opaque to X-rays, suspended within the fluid; and
 at least two electrodes on opposite sides of each envelope, configured to apply a respective field to the multiple particles in the each envelope, and wherein absent the respective field, the particles disperse throughout the fluid.

In a disclosed embodiment the at least two electrodes on opposite sides of each envelope include a first pair of electrodes on a first pair of opposite sides of the each envelope and a second pair of electrodes on a second pair of opposite sides of the each envelope, and the first and the second pairs of electrodes are mutually orthogonal.

In a further disclosed embodiment, for each envelope, the at least two electrodes on opposite sides of each envelope are individually addressable and switchable, and are configured to generate a respective field for each envelope so that each individual envelope in the array can be rendered transparent or opaque independently of other envelopes in the array.

There is further provided, according to an embodiment of the present invention, a method, including:
 providing an envelope transparent to X-rays;
 incorporating a fluid transparent to X-rays within the envelope;
 suspending multiple charged particles, opaque to X-rays, within the fluid; and
 positioning at least two electrodes on opposite sides of the envelope, wherein the at least two electrodes are configured to apply a field to the multiple particles, and wherein absent the field, the particles disperse throughout the fluid.

There is further provided, according to an embodiment of the present invention, a method, including:
 providing an array of envelopes transparent to X-rays;
 incorporating a fluid transparent to X-rays within the envelopes;
 suspending multiple charged particles, opaque to X-rays, within the fluid; and
 positioning at least two electrodes on opposite sides of each envelope, wherein the at least two electrodes are configured to apply a respective field to the multiple particles in the each envelope, and wherein absent the respective field, the particles disperse throughout the fluid.

The present disclosure will be more fully understood from the following detailed description of the embodiments thereof, taken together with the drawings, in which:

BRIEF DESCRIPTION OF THE DRAWINGS

FIG. 4 is a schematic illustration of an array of receptacles, according to an embodiment of the present invention; and FIGS. 5 and 6 are schematic illustrations of the operation of the array, according to an embodiment of the present invention.

DETAILED DESCRIPTION OF EMBODIMENTS

Overview

During a medical procedure using a fluoroscope, the physician performing the procedure may desire to indicate a specific region of a patient so that the region is visible on the fluoroscope image. The indication may typically be made by the physician, or another person, physically placing one or more fluoroscopically opaque markers at the specific region. Typically, the markers need to be removed at a later stage in the procedure. However, to correctly place, and remove, the markers interrupts the work flow of the physician.

Embodiments of the present invention solve this problem by providing fluoroscope markers that have adjustable opacity. In other words, a specific marker can be set to be fluoroscopically opaque, so as to be visible on a fluoroscope image, or to be fluoroscopically transparent, so as to be invisible on a fluoroscope image. Thus, once an opaque marker has been positioned, there is no need to physically remove it since the marker may be converted to a transparent marker.

In one embodiment, the marker comprises an array of envelopes, each envelope being transparent to X-rays and being filled with a fluid that is also transparent to X-rays. Multiple charged particles are suspended within the fluid. Around each envelope at least two electrodes, and typically four electrodes, are arranged on opposite sides of the envelope. The electrodes are configured to apply a field to the particles so that when a first field is applied the particles form a first layer within the envelope that renders the envelope opaque to X-rays, and when a second field is applied the particles form a second layer within the envelope that renders the envelope transparent to the X-rays.

DETAILED DESCRIPTION

Figure 1:
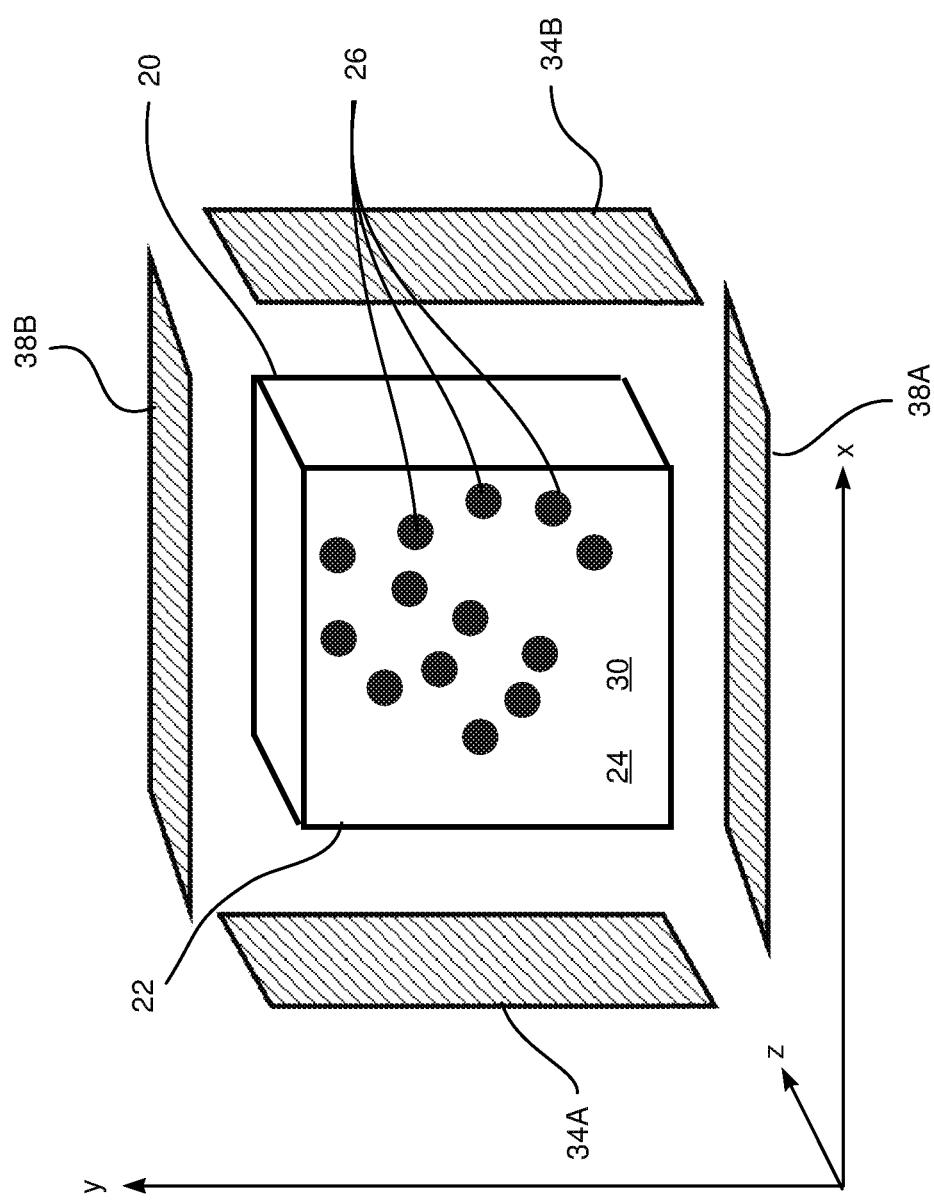
FIG. 1 is a schematic illustration of a receptacle, according to an embodiment of the present invention.

FIG. 1 is a schematic illustration of a receptacle 20, according to an embodiment of the present invention. Receptacle 20, has an outer, approximately cubic envelope that is transparent fluoroscopically. Typically envelope 22 is formed from biocompatible plastic, and may be transparent or opaque to visible radiation. The cubic envelope has a typical side of approximately 1 mm, although in some embodiments the side may be smaller or larger than this value. For clarity in the following description, edges of receptacle 20 are by way of example assumed to define a set of orthogonal xyz axes.

Receptacle 20 is filled with an inert, biocompatible dielectric, i.e., non-conductive, fluid 24, such as a paraffin liquid at room temperature, and for simplicity the fluid is herein assumed to comprise a liquid, and is also referred to herein as liquid 24. Liquid 24 is selected to be transparent to X-rays. Dispersed within the liquid are a plurality of particles 26, typically approximately spherical, which are formed comprising a material that is opaque to X-rays, such as barium sulfate, bismuth subcarbonate, or bismuth oxychloride. In addition, particles 26 are configured to have substantially the same density as liquid 24, so that the particles and the liquid together form a suspension 30. Receptacle 20 is typically sealed with suspension 30 contained within the receptacle.

Furthermore, particles 26 are also configured to carry a charge. To implement the charge carried by the particles, the particles may have a native charge, may be charged explicitly using a charge-control agent that is typically added to the particles to confer a surface charge, or may acquire a charge when suspended in dielectric liquid 24, and in the following description particles 26 are assumed, by way of example, to have a negative charge. Suspension 30 is thus an electrophoretic suspension.

In some embodiments particles 26 are Janus nanoparticles which have been coated with a charged polymer. An article "Synthesis, properties and applications of Janus nanoparticles," published in Nano Today 6 (3): June 2011 Pages 286-308, by Lattuada et al., describes the production of such particles, and is incorporated herein by reference. Cospheric LLC, of Santa Barbara, Calif., produce micro-particles, including Janus micro-particles that may be configured to be charged, as described above, so as to be suitable for use as particles 26.

Receptacle 20 has a first pair of electrodes 34A, 34B on sides of the receptacle that are orthogonal to the x-axis, and a second pair of electrodes 38A, 38B on sides of the receptacle that are orthogonal to the y-axis. Thus, the two pairs of electrodes are mutually orthogonal to each other. Typically the electrodes are formed on the outside of envelope 22, but for clarity in the figures, the electrodes are illustrated as being separate from the envelope. Material for the electrodes is selected to be transparent to X-rays.

Figure 2:
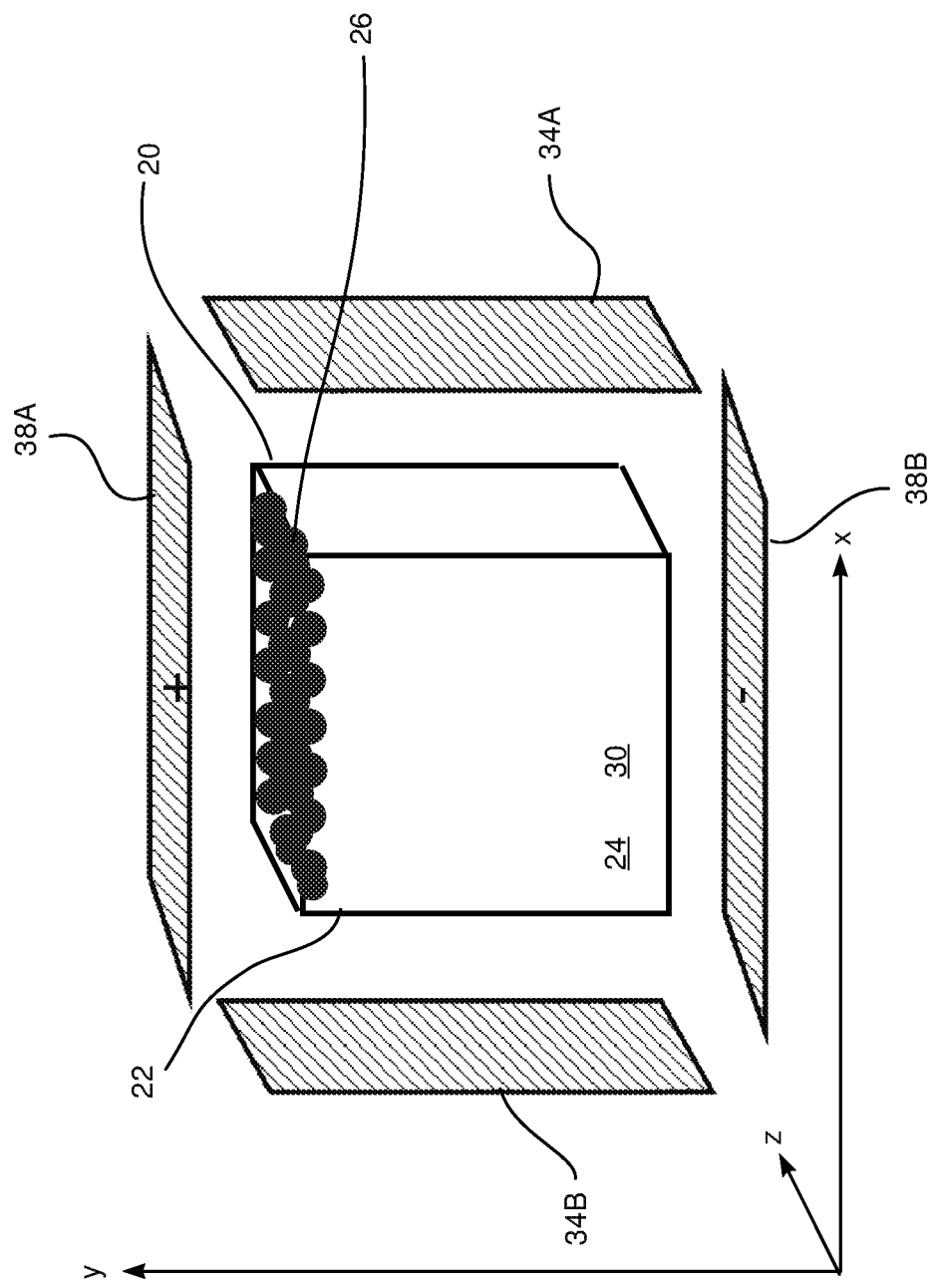
FIG. 2 illustrates the behavior of a suspension within the receptacle, according to an embodiment of the present invention.

FIG. 2 illustrates the behavior of suspension 30 when electrodes 38A, 38B have a positive and a negative charge on the electrodes, and when electrodes 34A, 34B are uncharged, according to an embodiment of the present invention. In this case electrodes 38A, 38B produce an electric field parallel to the y-axis, so that particles 26 are attracted towards the positive electrode, and form a generally planar layer on the interior surface of receptacle 20 that is in proximity to positively charged electrode 38A.

Figure 3:
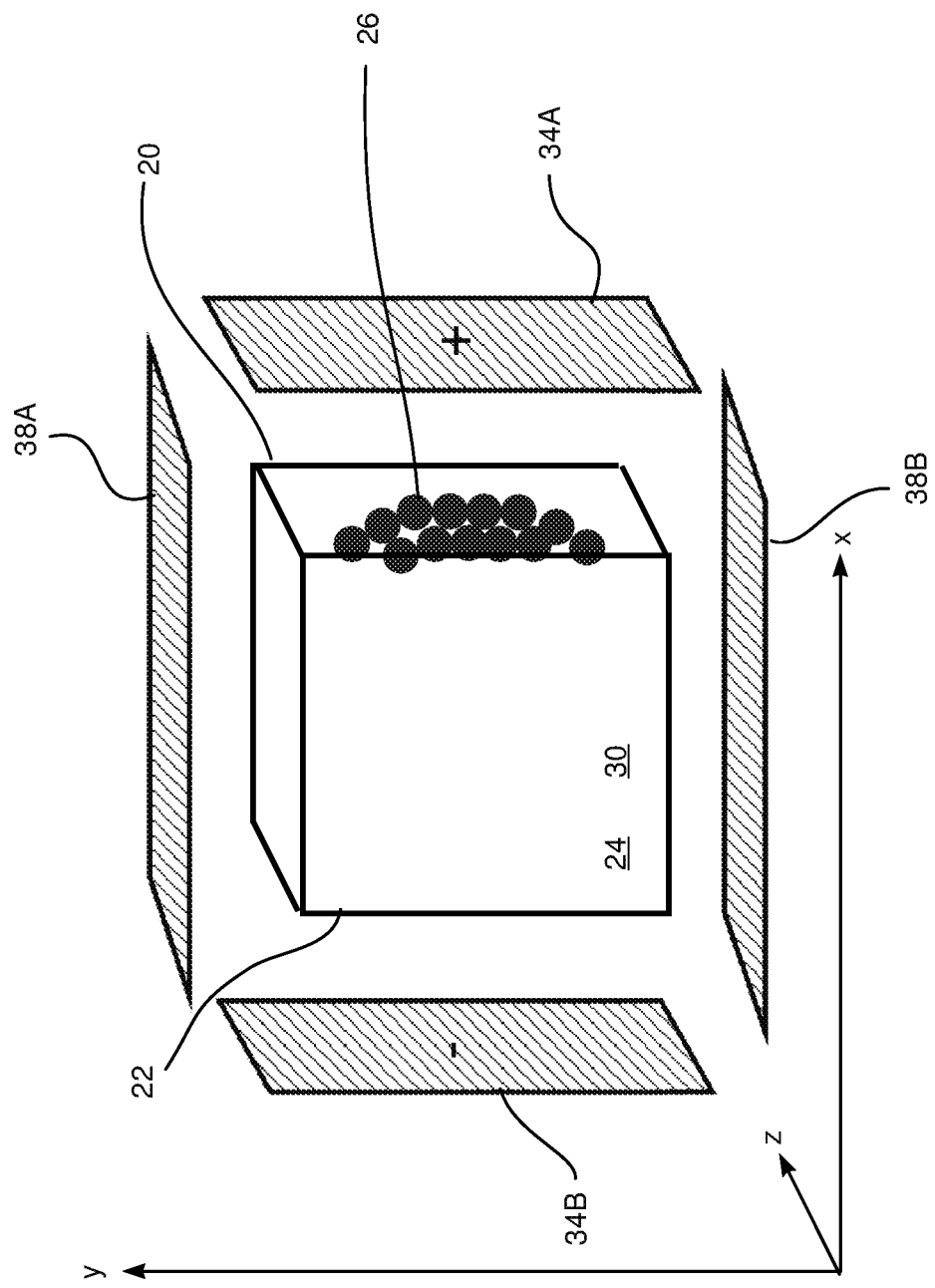
FIG. 3 illustrates the behavior of the suspension within the receptacle, according to an alternative embodiment of the present invention.

FIG. 3 illustrates the behavior of suspension 30 when electrodes 34A, 34B have a positive and a negative charge on the electrodes, and when electrodes 38A, 38B are uncharged, according to an embodiment of the present invention. Thus, electrodes 34A, 34B produce an electric field parallel to the x-axis. Particles 26 are attracted towards the positive electrode 34A, and form a generally planar layer on the interior surface of receptacle 20 that is in proximity to positively charged electrode 34A.

FIG. 4 is a schematic illustration of an array 50 of receptacles 20, according to an embodiment of the present invention. Array 50 is, by way of example, assumed to comprise a rectangular array that is one receptacle deep. An inset 54 illustrates two of receptacles 20 in more detail, and for clarity the inset shows the two receptacles in an exploded form. Also for clarity, electrodes 38A, 38B, formed on the receptacles, are not shown in the inset.

Electrodes 34A, 34B, of adjacent receptacles 20 are separated by insulators 60. Typically, all electrodes 34A of array 50 are connected together. Similarly all electrodes 34B of the array are connected together. However, insulators 60 ensure that electrodes 34A and 34B are electrically insulated from each other. Although not shown in the diagram, all electrodes 38A are connected together, and all electrodes 38B are connected together.

FIGS. 5 and 6 are schematic illustrations of the operation of array 50, according to an embodiment of the present invention. The diagrams illustrate a cross-section of array 50, and the array is assumed to be placed between an X-ray source 70 and an X-ray detector 72, which are elements of a fluoroscope. Typically array 50 is configured as a flexible pad which may be placed on a patient undergoing a medical procedure. During the procedure the fluoroscope is typically used to image a patient, who is also between the source and the detector. The signals from the detector are used to generate an X-ray image of the patient, which is displayed on a screen 74, by methods which are well-known in the X-ray imaging arts. (For simplicity the patient is not illustrated in the diagrams.)

FIG. 5 illustrates the image on the screen 74 when an electric field is applied to the array along the y-axis, e.g., if electrodes 38A, 38B respectively have positive and negative charges, and if electrodes 34A, 34B are uncharged. In this case receptacles 20 of array 50 are generally opaque to the X-rays from the X-ray source, so that the screen registers the array as an X-ray opaque object.

FIG. 6 illustrates the image on the screen when an electric field is applied to the array along the x-axis, e.g., if electrodes 34A, 34B respectively have positive and negative charges, and if electrodes 38A, 38B are uncharged. In this case receptacles 20 of array 50 are generally transparent to the X-rays from the X-ray source, so that the screen registers the array as an X-ray transparent object.

It will be understood from the above description that array 50 may be configured as a switchable X-ray marker for the type of procedure described above. I.e., array 50 may be configured to be opaque, or transparent by simply changing the charges on electrodes 34A, 34B, 38A, and 38B.

The description above has assumed that array 50 is configured so that all receptacles 20 of the array may be switched to be X-ray transparent, or so that all receptacles 20 may be switched to be opaque. This is because in array 50 there is no way of individually changing selected receptacles 20 to be transparent or opaque.

Embodiments of the present invention include arrays of receptacles 20 wherein the x-axis fields and the y-axis fields on the receptacles are individually addressable and switchable. For these types of arrays at least one set of electrodes for the x-axis field and at least one set of electrodes for the y-axis field are not connected to other corresponding electrodes. For example, each electrode 34A in an array may be configured to be individually addressable, while all electrodes 34B may be connected together, typically to a ground. Similarly each electrode 38A in the array may be configured to be individually addressable, while all electrodes 38B may be connected together, also typically to ground. Such an arrangement enables each individual receptacle in the array to be rendered transparent or opaque to X-rays, so that, for example the array may be used to provide a switchable label or diagram or icon on the X-ray image.

The description above has assumed for simplicity that receptacles 20 are in the form of cubes. However, it will be understood that other shapes of receptacles are comprised within the scope of the present invention. For example, rather than the receptacles being in the form of cubes, they may be in the form of parallelepipeds, or of volumes having curved sides, including ellipsoidal or spherical volumes. Furthermore, the receptacles do not all need to be the same shape or to have the same dimensions, so that, for example, some arrays may have combinations of parallelepipeds and/or ellipsoids having different sizes and/or different shapes.

Regardless of the shape of a given receptacle, it will be understood that the electrodes that are formed on the receptacle may be configured to enable the x-axis field and the y-axis field to be independently switchable. For example, in the case of a spherical receptacle, four isolated electrodes may be formed about the receptacle, two of the electrodes being at the "top" and the "bottom" of the sphere, and two electrodes being at opposite "sides" of the sphere.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus having fluoroscopic markers that are adjustably opaque or transparent on a fluoroscopic image, comprising:
   a receptacle transparent to X-rays;
   an electrophoretic suspension within the receptacle said electrophoretic formed of a liquid transparent to X-rays and multiple charged particles opaque to X-rays suspended within the liquid; and
   at least two switchable electrodes on opposite sides of the receptacle, configured to apply a field to the particles, wherein absent the field, the particles disperse throughout the liquid and wherein the presence or absence of charge on the switchable electrodes determines whether the receptacle is transparent or opaque to x-rays from an x-ray source.

2. The apparatus according to claim 1, wherein the field applied by the at least two switchable electrodes attracts the multiple charged particles to form a layer within the envelope so as to render the receptacle opaque to the X-rays.

3. The apparatus according to claim 1, wherein the field applied by the at least two switchable electrodes attracts the multiple charged particles to form a layer within the envelope so as to render the receptacle transparent to the X-rays.

4. The apparatus according to claim 1, wherein the at least two switchable electrodes on opposite sides of the receptacle comprise a first pair of switchable electrodes on a first pair of opposite sides of the receptacle and a second pair of switchable electrodes on a second pair of opposite sides of the receptacle.

5. The apparatus according to claim 4, wherein the first pair of switchable electrodes is configured to apply a first field so as to attract the multiple charged particles to form a first layer within the receptacle that renders the receptacle opaque to the X-rays, and wherein the second pair of switchable electrodes is configured to apply a second field so as to attract the multiple charged particles to form a second layer within the receptacle that renders the receptacle transparent to the X-rays.

6. Apparatus having fluoroscopic markers that are adjustably opaque or transparent on a fluoroscopic image, comprising:
   an array of receptacles transparent to X-rays;
   an electrophoretic suspension within the receptacles said electrophoretic suspension formed of a liquid transparent to X-rays and multiple charged particles opaque to X-rays
   at least two switchable electrodes on opposite sides of each receptacle, configured to apply a respective field to the multiple particles in the each receptacle, and
   wherein absent the respective field, the particles disperse throughout the liquid and wherein the presence or absence of charge on the switchable electrode determines whether the receptacle is transparent or opaque to x-rays from an x-ray source.

7. The apparatus according to claim 6, wherein the at least two switchable electrodes on opposite sides of each receptacle comprise a first pair of switchable electrodes on a first pair of opposite sides of the each receptacle and a second pair of switchable electrodes on a second pair of opposite sides of the each receptacle.

8. The apparatus according to claim 6, wherein, for each receptacle, the at least two switchable electrodes on opposite sides of each receptacle are individually addressable and switchable, and are configured to generate a respective field for each receptacle so that each individual receptacle in the array can be rendered transparent or opaque independently of other receptacles in the array.

9. A method for producing a receptacle that is transparent or opaque to x-rays from an x-ray source, comprising:
providing an receptacle transparent to X-rays;
providing an electrophoretic suspension within the receptacle said electrophoretic suspension formed of a liquid transparent to X-rays and multiple charged particles, opaque to X-rays suspended and
positioning at least two switchable electrodes on opposite sides of the receptacle,
wherein the at least two switchable electrodes are configured to apply a respective field to the multiple particles, and wherein absent the field, the particles disperse throughout the liquid, and wherein the presence or absence of charge on the switchable electrodes determines whether the receptacle is transparent or opaque to x-rays from an x-ray source.

10. The method according to claim 9, wherein the field applied by the at least two switchable electrodes attracts the multiple charged particles to form a layer within the receptacle so as to render the receptacle opaque to the X-rays.

11. The method according to claim 9, wherein the field applied by the at least two switchable electrodes attracts the multiple charged particles to form a layer within the receptacle so as to render the receptacle transparent to the X-rays.

12. The method according to claim 9, wherein the at least two switchable electrodes on opposite sides of the receptacle comprise a first pair of switchable electrodes on a first pair of opposite sides of the receptacle and a second pair of switchable electrodes on a second pair of opposite sides of the receptacle.

13. The method according to claim 12, wherein the first pair of switchable electrodes is configured to apply a first field so as to attract the multiple charged particles to form a first layer within the receptacle that renders the receptacle opaque to the X-rays, and wherein the second pair of switchable electrodes is configured to apply a second field so as to attract the multiple charged particles to form a second layer within the receptacle that renders the receptacle transparent to the X-rays.

14. A method for producing an array of receptacles that are transparent or opaque to x-rays from an x-ray source, comprising:
providing an array of receptacle transparent to X-rays;
providing an electrophoretic suspension within the envelope said electrophoretic suspension formed of a liquid transparent to X-rays within the receptacles;
suspending multiple charged particles, opaque to X-rays, within the liquid; and
positioning at least two switchable electrodes on opposite sides of each receptacle, wherein the at least two switchable electrodes are configured to apply a respective field to the multiple particles in the each receptacle, wherein absent the respective field, the particles disperse throughout the liquid and wherein the presence or absence of charge on the switchable electrodes determine whether the receptacle is transparent or opaque to x-rays from an x-ray source.

15. The method according to claim 14, wherein the at least two switchable electrodes on opposite sides of each receptacle comprise a first pair of switchable electrodes on a first pair of opposite sides of the each receptacle and a second pair of switchable electrodes on a second pair of opposite sides of the each receptacle.

16. The method according to claim 14, wherein, for each receptacle, the at least two switchable electrodes on opposite sides of each receptacle are individually addressable and switchable, and are configured to generate a respective field for each receptacle so that each individual receptacle in the array can be rendered transparent or opaque independently of other receptacles in the array.

17. The apparatus according to claim 1 or claim 6, wherein the liquid and the multiple charged particles have substantially the same density.

18. The method according to claim 9 or claim 14, wherein the liquid and the multiple charged particles have the same density.

19. The apparatus according to claim 1 or claim 6, wherein the multiple particles comprise a material selected from the group consisting of barium sulfate, barium carbonate and bismuth oxychloride.

20. The method according to claim 9 or claim 14, wherein the multiple particles comprise a material selected from the group consisting of barium sulfate, barium carbonate and bismuth oxychloride.

21. The apparatus according to claim 4 or claim 7, wherein the first and the second pair of switchable electrodes are mutually orthogonal.

22. The method according to claim 12 or 15, wherein the first and second pair of switchable electrodes are mutually orthogonal.

* * * * *